(12) United States Patent
Takai et al.

(10) Patent No.: US 7,332,644 B2
(45) Date of Patent: Feb. 19, 2008

(54) NON-HUMAN ANIMAL MODEL OF OLIGODENDROCYTE DEVELOPMENTAL DISORDER

(75) Inventors: Toshiyuki Takai, Sendai (JP); Hiroaki Aso, Tokyo (JP); Michihiro Fujiwara, Fukuoka (JP)

(73) Assignee: Japan Science and Technology Agency (JP)

( * ) Notice: Subject to any disclaimer, the term of this patent is extended or adjusted under 35 U.S.C. 154(b) by 218 days.

(21) Appl. No.: 10/712,118

(22) Filed: Nov. 13, 2003

(65) Prior Publication Data

US 2005/0210538 A1    Sep. 22, 2005

Related U.S. Application Data

(63) Continuation-in-part of application No. PCT/JP02/04405, filed on May 2, 2002.

(30) Foreign Application Priority Data

May 16, 2001    (JP) ............................. 2001-146338

(51) Int. Cl.
*A01K 67/00* (2006.01)
*A01K 67/033* (2006.01)
*A01K 67/027* (2006.01)
*C07H 21/02* (2006.01)
*C07H 21/04* (2006.01)

(52) U.S. Cl. ............................. 800/9; 800/18; 536/23.1
(58) Field of Classification Search .................... 800/9, 800/18; 536/23.1
See application file for complete search history.

(56) References Cited

U.S. PATENT DOCUMENTS

2004/0045041 A1* 3/2004 Vivier et al. .................. 800/3

FOREIGN PATENT DOCUMENTS

WO    WO 96 09386    3/1996
WO    WO 97 07200    2/1997

OTHER PUBLICATIONS

Jacks et al. 1992 Nature, 359: 295-300.*
Kuehn et al., 1987 Nature, 326: 295-298.*
Jaenisch, 1988 Science, 240: 1468-1474.*
Murray, et al., 1999, Transgenic Animals in Agriculture, CAB International: Oxon, pp. 58-61.*
Levine et al., 2001, Trends in Neuroscience, 24: 39-47.*
Osterhout et al., 1997, J. of Neuroscience, 17: 9122-9132.*
Porter and Tennekoon, 2000, Mental Retardation and Developmental Disabilities Research Reviews, 6: 47-58.*
Geyer et al., 2002, Molecular Psychiatry, 7: 1039-1053.*
Bakker et al., 2000, Immunity, 13: 345-353.*
Tomasello et al., 2000, Immunity, 13: 355-364.*
Goedert et al., 1998, Neuron, 21: 955-958.*
Emre, 2003, The Lancet, 2: 229-237.*
Zink et al., 1999, FEMS Immunology and Medical Microbiology 26: 233-241.*
Corfas et al., 2004, Nature Neuroscience, 7: 575-580.*
Takai, T., et al., "FcR γ Chain Deletion Results in Pleiotrophic Effector Cell Defects," Cell, vol. 76, 1994, pp. 519-529.
Paloneva, J., et al., "CNS manifestations of Nasu-Hakola disease," Neurology, vol. 56, No. 11, 2001, pp. 1552-1558.
Paloneva, J., et al., "Loss-of-function mutations in TYROBP (DAP12) result in a presenile dementia with bone cysts," Nature Genetics, vol. 25, No. 3, 2000, pp. 357-361.
American Journal of Human Genetics, vol. 67, No. 4 (supplement 2), 2000, p. 177.
Eng et al. "The Relationship Between Specific RET Photooncogene Mutations and Disease Phenotype in Multiple Endocrine Neoplasia Type 2," JAMA Nov. 20, 1996, vol. 276, No. 19.
Chang et al., "Cutting Edge: KAP10. a Novel Transmembrane Adapter Protein Genetically Linked to DAP12 but with Unique Signaling Properties," J. Immunol. (1999) 163: 4651-4654.
Dupouey et al., "Immunochemical Studies of Myelin Basic Proteins in Shiverer Mouse Devoid of Major Dense Line of Myelin," Neuroscience Letter, (1979) 12: 113-118.
Griffiths et al., "Axonal Swellings and Degeneration in Mice Lacking the Major Proteolipid of Myelin," Science (1998) 280: 1610-1613.
Hakola et al., "Neuropsychiatric And Genetic Aspects Of a New Hereditary Disease Characterized By Progressive Dementia And Lipomembranous Polycystic Osteodysplasia," Acta Phychiatrica Scandinavica Supplementum (1972) 232:1-173.
Kaelin et al., "Expression Cloning of a cDNA Encoding a Retinoblastoma-Binding Protein with E2F-like Properties," Cell (1992) vol. 70, 351-364.
Kobayashi et al., "Hypothalamic haemorrhage and thalamas degeneration in a case of Nasu-Hakola disease with hallucinatory symptoms and central hypothermia," Neuropathology and Applied Neurobiology (2000). 26: 98-101.
Kodsi and N. R. Swerdlow, "Regulation of Prepulse Inhibition by Ventral Pallidal Projections," Brain Research Bulletin (1997) vol. 43, No. 2, pp. 219-228, 1997.

(Continued)

Primary Examiner—Anne Marie Wehbe'
Assistant Examiner—Joanne Hama
(74) Attorney, Agent, or Firm—Frommer Lawrence & Haug LLP; Thomas J. Kowalski; Deborah L. Lu

(57) ABSTRACT

The objects of the present invention is to provide a preventive method for the progress of neuropsychiatric disorders, a therapeutic agent for neuropsychiatric disorders, a screening method thereof, and a therapeutic method through the analysis of the mechanisms leading to neuropsychiatric disorders such as Nasu-Hakola diseases and the like. The non-human animal model of oligodendrocytes developmental disorders was generated by making the DAP12 gene function deficient on its chromosome. The DAP12 knockout mouse develops myelination disorders including hypomyelinosis in the brain, particularly in the frontal head and the thalamus, further leading to neuropsychiatric disorders such as Nasu-Hakola disease and the like with aging. The screening method for a therapeutic agent, the diagnostic method, and the therapeutic method, wherein the DAP12 knockout mouse developing these disorders are used, have been developed.

6 Claims, 6 Drawing Sheets

OTHER PUBLICATIONS

Lanier et al., "Association of DAP12 with Activating CD94/NKG2C Cell Receptors," Immunity (1998) vol. 8, 693-701.

Lanier et al., "Immunoreceptor DAP12 bearing a tyrosine-based activation Motif is involved in activating NK cells," Nature (1998) vol. 391: 703-707.

Mason et al., "Cutting Edge: Characterization of an Associated 16-kDa Tyrosine Phosphoprotein Required for Ly-49D Signal Transduction," J. Immunol. (1998) 160:4148-4152.

Nasu et al., "A Lipid Metabolic Disease—"Membranous Lipodystrophy" An Autopsy Case Demonstrating Numberous Peculiar Membrane Structures Composed of Compound Lipid in Bone and Bone Marrow and Various Adipose Tissues," Acta Path. Jap. (1973) 23(3): 539-558.

Olcese et al., "Human Killer Cell Activatory Receptors for MIIC Class I Molecules Are Included in A Multimeric Complex Expressed by Natural Killer Cells," The American Association of Immunologist (1997) 158:5083-5086.

Romanski et al., "Equipotentiality of Thalamo-Amygdala and Thalamo-Cortico-Amygdala Circuits in Auditory Fear Conditioning," The Journal of Neuroscience (1992) 12(11): 4501-4509.

Seiwa et al., "Fyn tyrosine kinase participates in the compact myelin sheath formation in the central nervous system," Neuroscience Research (2000) 37(1):21-31.

Shinohara et al., "A case of Nasu-Hakola's disease with T2-weighted MRI finding of reduced signal intensity in the thalamus and putamen," Clin. Neurol. (2002) 32: 444-446.

Smith et al., "Cutting Edge: Ly-49D and Ly-49H Associate with Mouse DAP12 and form Activating Receptors," J. Immunol. (1998) 161: 7-10.

Sommer et al., "Monoclonal Antibodies (O1 to O4) to Oligodendrocyte Cell Surfaces: An Immunocytological Study in the Central Nervous System," Developmental Biology (1981) vol. 83: 311-327.

Verloes et al., "Nasu-Hakola syndrome: polycystic lipomembranous osteodysplasia with sclerosing leucoencephalopathy and presenile dementia," F. Med. Genet. (1997) vol. 34:753-757.

Wu et al., "Lateral geniculate spikes, muscle atonia and startle response elicited by auditory as a function of stimulus parameters and arousal state," Brain Research (1989) 499(1): 7-17.

Wu et al., "An Activating Immunoreceptor Complex Formed by NKG2D and DAP10," Science (1999) vol. 285:730-732.

Schmitt et al. Altered thalamic membrane phospholipids in schizophrenia: a postmortem study. Biol Psychiatry 56: 41-45, 2004.

Humphrey Mary Beth et al: "The signaling adapter protein DAP12 regulates multinucleation during osteoclast development." Journal of Bone and Mineral Research: The Official Journal of the American Society for Bone and Mineral Research. Feb. 2004, vol. 19, No. 2, Feb. 2004, pp. 224-234, XP002413095 ISSN: 0884-0431.

Nataf Serge et al: "Brain and bone damage in KARAP/DAP12 loss-of-function mice correlate with alterations in microglia and osteoclast lineages" American Journal of Pathology, vol. 166, No. 1, Jan. 2005, pp. 275-286, XP002413094 ISSN: 0002-9440.

Kaifu Tomonori et al: "Osteopetrosis and thalamic hypomyelinosis with synaptic degeneration in DAP12-deficient mice." The Journal of Clinical Investigation. Feb. 2003, vol. 111, No. 3, Feb. 2003, pp. 323-332, XP002412551 ISSN: 0021-9738.

Colonna Macro: "DAP12 signaling: from immune cells to bone modeling and brain myelination." The Journal of Clinical Investigation. Feb. 2003, vol. 111, No. 3, Feb. 2003, pp. 313-314, XP002412550 ISSN: 0021-9738.

* cited by examiner

NON-HUMAN ANIMAL MODEL OF OLIGODENDROCYTE DEVELOPMENTAL DISORDER

REFERENCE TO RELATED APPLICATIONS

This application is a continuation-in-part of International Application PCT/JP02/04405 filed on May 2, 2002 and published as WO 02/091820 on Nov. 21, 2002, which application claims priority from Japanese Application No. 2001-146338, filed on May 16, 2001. Each of the foregoing applications, and each document cited or referenced in each of the foregoing applications, including during the prosecution of each of the foregoing applications and ("application cited documents"), and any manufacturer's instructions or catalogues for any products cited or mentioned in each of the foregoing applications and articles and in any of the application cited documents, are hereby incorporated herein by reference. Furthermore, all documents cited in this text, and all documents cited or referenced in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

FIELD OF THE INVENTION

The present invention relates to a non-human animal model of oligodendrocyte developmental disorder whose DAP12 (DNAX Activation Protein 12) gene function is deficient on its chromosome; a screening method for a developmental promoter or a developmental suppressor of oligodendrocytes, or a promoter or a suppressor of myelinogenesis, wherein the non-human animal model of oligodendrocyte developmental disorder is used; a screening method for a therapeutic agent for neuropsychiatric disorders; and a diagnostic method for neuropsychiatric disorders.

BACKGROUND OF THE INVENTION

DAP12 (DNAX Activation Protein 12) is indicated to be a transmembrane protein containing an activation motif, ITAM, which binds to ZAP-70 or Syk through phosphorylation. It is known that DAP12 is encoded by a single-copy gene located on the 19q13.1 in humans and also exists in mice. It is also known that mRNAs of the DAP12 are largely expressed in monocytes, dendritic cells, and natural killer cells, and that DAP12 is not only involved in activated signaling of a KAR group, but also associates with a human signal regulatory protein (SIRP) β1, a human or a murine myeloid DAP12-associating lectin (MDL)-1, and a triggering receptor expressed on myeloid cells (TREM). It is reported that DAP12 also associates with KAR molecules, which belong to the C-type lectin family, such as CD94/NKG2C and the like, and performs its function (Immunity 8, 693-701, 1998; J. Immunol. 161, 7-10, 1998; J. Immunol. 160, 4148-52, 1998).

Polycystic lipomembranous osteodysplasia with sclerosing leukoencephalopathy, also known as Nasu-Hakola disease (Suppl. 232, 1-173, 1972; Acta Pathol. Jpn. 23, 539-558, 1973; J. Med. Genet. 34, 753-757, 1977) is a central nervous system disorder found in Japan and Finland. In addition to the formation of bone cysts, patients of Nasu-Hakola disease develop psychotic symptoms, such as personality changes, inevitably progressing to pre-senile dementia. The mutation found in Finnish patients is a 5.3 kb deletion in the DAP12 [KARAP (Killer activating receptor associated protein)/TYROBP (protein tyrosine kinase binding protein)] locus, while another defect in Japanese patients is a single-nucleotide deletion in the third exon of the gene. Both are known to be caused by the loss of function of DAP12, a membrane adaptor protein (J. Immunol. 158, 5083-5086, 1997; Nature 391, 703-707, 1998) found initially in the immune system (Nature Genet. 25, 357-361, 2000). However, it has not yet known whether psychotic symptoms are caused by the deficiency of DAP12.

On the other hand, in an animal model of dementia, only methods for inducing cerebral ischemia or accumulating amyloid protein have been developed, and the utility values of such model animals as a base for analyzing the mechanisms progressing to dementia and for preventing the progression of dementia have not been efficient. It has been known in recent years that the deficiency of DAP12 induces the onset of neuropsychiatric disorders progressing to juvenile dementia called Nasu-Hakola disease (Nature Genet. 25, 357-361, 2000). However, the fundamental cause has not been verified, and it is not known whether the frontal lobe- and thalamus-specific dysmyelination occurs in DAP12 deficient mice that show symptoms of schizophrenia.

The aforementioned Nasu-Hakola disease is a recessive hereditary disease, which is fatal and inevitably progressing to presenile dementia following the formation of bone cysts and neuropsychiatric disorders. The object of the present invention is to provide the following: a non-human animal model of oligodendrocyte developmental disorder whose DAP12 (DNAX Activation Protein 12) gene function is deficient on its chromosome; a screening method for a developmental promoter or a developmental suppressor of oligodendrocytes, or, a promoter or a suppressor of myelinogenesis, wherein the non-human animal model of oligodendrocyte developmental disorder is used; a screening method for a therapeutic agent for neuropsychiatric disorders; a diagnostic method for neuropsychiatric disorders, which enable to develop a preventive method for the progress of neuropsychiatric disorders and a therapeutic method for neuropsychiatric disorders by analyzing the mechanisms progressing to neuropsychiatric disorders such as Nasu-Hakola disease, dementia, schizophrenia, schizotypal personality disorders, obsessive-compulsive disorders, Huntington's disease and Tourette's syndrome, etc.

The present inventors have analyzed the physiological function of DAP12, generated a mouse whose DAP12 gene function is deficient on its chromosome, namely a DAP12 knockout mouse, and examined the brain. The present inventors have found that demyelination, namely myelination disorder including hypomyelinosis, can be seen particularly in the frontal head and thalamus, and that this disorder is attributed to the inhibition of differentiation, development, intracerebral transfer in the cell due to the deficiency of DAP12 in oligodendrocytes that plays a role of myelinogenesis. The present inventors have further found that deficiency can be seen in the reflective power, despite that muscle and the like are normal by the behavioral analysis of the above-mentioned DAP12 knockout mouse, and clarified that psychotic symptoms similar to schizophrenia can be seen with aging.

SUMMARY OF THE INVENTION

The present invention relates to a non-human animal model of oligodendrocyte developmental disorders, wherein the non-human animal comprises a deficiency in chromosomal DAP12 (DNAX Activation Protein 12) gene function, and shows an oligodendrocyte developmental disorder. The oligodendrocyte developmental disorder can be a myelinogenesis developmental disorder or a neuropsychiatric disorder. The neuropsychiatric disorder can be Nasu-Hakola disease, dementia, schizophrenia, schizotypal personality disorders, obsessive-compulsive disorders, Huntington's disease or Tourette's syndrome and the non-human animal can be a mouse.

The invention further comprehends a screening method for a developmental promoter or a developmental suppressor of oligodendrocytes, wherein a test substance is administered to the non-human animal model of oligodendrocytes developmental disorders disclosed herein, or a test substance is contacted with a tissue, an organ, or a cell derived from the animal. The screening methods further comprise measuring and assessing the expression of myelin basic protein in the non-human animal model or tissues, organs, or cells derived therefrom. The screening method of the invention also provides for measuring and assessing the development of myelinogenesis or the extent of demyelination in the non-human animal, as well as measuring and assessing acoustic stimuli and/or acoustic prepulse inhibition of the non-human animal.

The present invention further relates to a screening method for a developmental promoter or a developmental suppressor of oligodendrocytes, wherein a non-human animal comprises a deficiency in chromosomal DAP12 gene function is compared to a wild-type non-human animal, which can be a mouse. The screening method of the invention also provides for a promoter or a suppressor of myelinogenesis, as well as a developmental promoter or a developmental suppressor of oligodendrocytes that can be obtained by the aforementioned screening method. Additionally, a promoter or a suppressor of myelinogenesis can also be obtained by the screening methods of the present invention.

The invention also comprehends a screening method for a therapeutic composition for neuropsychiatric disorders, wherein the non-human animal model of oligodendrocyte developmental disorders is used for the screening of a therapeutic composition. Therapeutic compositions for neuropsychiatric disorders that can be obtained by the screening method for a therapeutic agent for neuropsychiatric disorders are also provided. The invention further comprises a diagnostic method for neuropsychiatric disorders, wherein symptoms of the non-human animal model of oligodendrocyte developmental disorders are used to diagnose the neuropsychiatric disorder.

BRIEF DESCRIPTION OF THE FIGURES

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings in which.

DETAILED DESCRIPTION OF THE INVENTION

Figure 1:
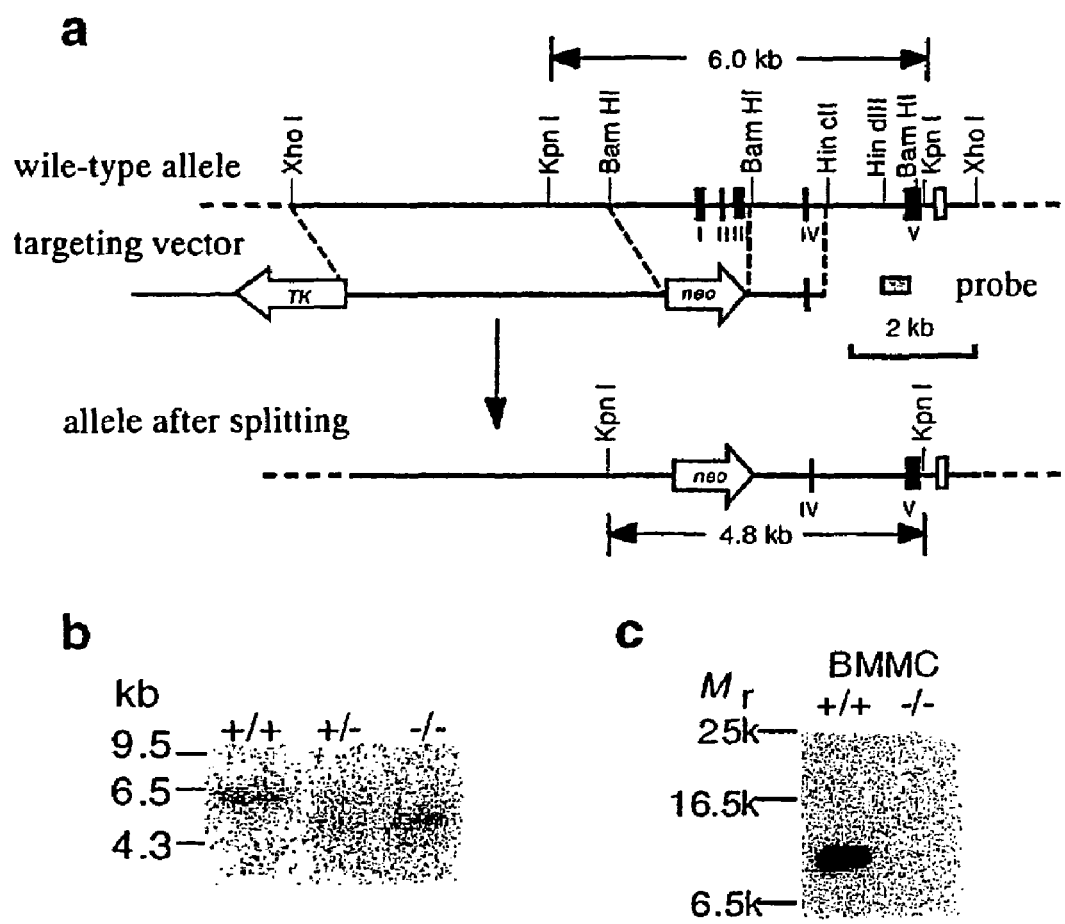
FIG. 1 shows gene maps of the DAP12 knockout mouse and the wild-type mouse of the present invention, and the results of PCR method and Southern blotting in each mouse.

For ease of reference a summary of the accompanying sequence listings is given below:

SEQ ID NO:1 shows an oligonucleotide primer sequence corresponding to a portion of the DAP12 gene.

SEQ ID NO:2 is another oligonucleotide primer sequence of a portion of the DAP12 gene.

SEQ ID NO:3 shows an oligonucleotide primer sequence corresponding to a portion of the DAP10 gene.

SEQ ID NO:4 is another oligonucleotide primer sequence of a portion of the DAP10 gene.

The non-human animal model of oligodendrocytes developmental disorders of the present invention is a non-human animal, wherein the development of oligodendrocytes are disordered due to a deficiency in DAP12 (DNAX activation protein 12) gene function on the chromosome. In the non-human animal, the expression of myelin basic protein is reduced, and developmental disorder of myelinogenesis in central nervous system is initiated, or neuropsychiatric disorders, such as, but not limited to Nasu-Hakola disease, dementia, schizophrenia, schizotypal personality disorders, obsessive-compulsive disorders, Huntington's disease and Tourette's syndrome, are induced with aging. The above-mentioned non-human animal whose DAP12 gene function is deficient on its chromosome means a non-human animal whose whole or part of endogenous gene encoding DAP12 is inactivated by gene mutations such as deletion, deficiency, substitution, etc., and whose DAP12-expressing function is lost. Although the non-human animals of the present invention can be particularly exemplified by rodents such as mice, rats, and others, the examples will not be limited to these animals. Other animals that can be advantageously used include, but are not limited to guinea pigs, monkeys, cats, dogs, horses, cattle, or rabbits.

The wild-type non-human animal of the present invention means an animal of the same species as the above-mentioned non-human animal; whose DAP12 gene function is not deficient and its littermate can be preferably exemplified. It is preferable to simultaneously use the DAP12 deficient type and its wild-type littermate among these homozygous non-human animals, since accurate comparative experiments can be carried out on the individual level. A preferred non-human animal model of oligodendrocytes developmental disorders of the present invention can be exemplified by a DAP12 knockout mouse, and the wild-type non-human animal can be exemplified by a wild-type littermate thereof respectively. It will be explained in the following with the case wherein the non-human animal is a mouse as an example.

A mouse whose DAP12 gene function is deficient on its chromosome, namely, a DAP12 knockout mouse ($DAP12^{-/-}$) can be generated by the method as described previously (Cell 76, 519-529, 1994), or the like. In concrete terms, DAP12 gene is screened by using a gene fragment obtained by a method, such as PCR method or the like, from the mouse genomic library. The screened DAP12 gene, in whole or in part is, for instance, substituted with a marker gene such as a neomycin-resistance gene using a recombinant DNA technology. A gene such as the diphtheria toxin A fragment (DT-A) gene, the herpes simplex virus thymidine kinase (HSV-tk) gene, or other suitable gene or gene fragment, is introduced onto the 5'-end to generate a targeting vector. Thus, the generated targeting vector is linearized and introduced into ES cells with electroporation, calcium phosphate precipitation, liposome-mediated delivery, microinjection, DEAE-dextran transfection, among other methods well-known in the art to facilitate homologous recombination. Among such homologous recombinants, ES cells showing resistance to antibiotics such as but not limited to G418, gancyclovir (GANC), tetracycline, doxycycline, ampicillin, chloramphenicol, puromycin, gentamicin, bleomycin, hygromycin, kanamycin, mitomycin, paromomycin, polymyxin, puromycin, rifampicin, spectinomycin, tylosin, and zeocin are selected. It is preferable to confirm whether the ES cells selected herein are the recombinants of interest by Southern blotting, polymerase chain reaction, or other methods familiar to those skilled in the art.

The above-mentioned recombinant ES cells are microinjected into a murine blastocyst, and the recombinant blastocyst is placed back to the recipient mouse to generate a chimeric mouse. A heterozygous mouse can be obtained by intercrossing the chimeric mouse and a wild type mouse. By further intercrossing the heterozygous mice, a DAP12 knockout mouse can be obtained. A DAP12 gene deficiency on its chromosome in the DAP12 knockout mouse can be examined by a method wherein DNA is isolated from the tail of a mouse obtained by the above-mentioned method and examined by Southern blotting, or a method wherein a protein extracted from a marrow mast cell of the mouse is examined by immunoblot analysis. The presence or absence of the DAP12 gene can also be detected by quantitative PCR, in situ hybridization, and other techniques that are within the purview of the skilled artisan.

The non-human animal model of oligodendrocyte developmental disorders of the present invention is useful for the following models: a model wherein a developmental disorder of oligodendrocytes occurs; a model wherein a developmental disorder of myelinogenesis in central nervous system occurs; a model wherein the process of myelinogenesis is investigated; a model wherein the onset processes of the diseases caused by oligodendrocyte developmental disorders, and neuropsychiatric disorders such as dementia caused by dysmyelination are investigated. Using the non-human animal model of myelinogenesis developmental disorders, it is possible to screen an effective agent for treating the diseases attributed to oligodendrocyte developmental disorders, for instance, neuropsychiatric disorders such as Nasu-Hakola disease, dementia, schizophrenia, schizotypal personality disorders, obsessive-compulsive disorders, Huntington's disease and Tourette's syndrome, etc, namely a developmental promoter or a developmental suppressor of oligodendrocytes, a promoter or a suppressor of myelinogenesis and the like.

The screening method for a developmental promoter or a developmental suppressor of oligodendrocytes, a promoter or a suppressor of myelinogenesis and others of the present invention can be exemplified by the following: a method wherein a test substance is administered to the non-human animal model of oligodendrocyte developmental disorders of the present invention; and a method wherein a tissue, an organ, or a cell derived from the non-human animal model of oligodendrocytes developmental disorders of the present invention is contacted with a test substance. The method wherein a tissue, an organ, or a cell derived from the non-human animal model of oligodendrocyte developmental disorders is contacted with a test substance, can be particularly exemplified by, for instance, a method wherein a tissue, an organ, or a cell derived from a non-human animal model of oligodendrocyte developmental disorders, such as the aforementioned DAP12 knockout mouse is contacted with a test substance, and the expression of myelin basic protein in the cells is measured and assessed.

The method wherein a test substance is administered to the non-human animal model of oligodendrocyte developmental disorders can be particularly exemplified by the following, but they are not limited to these examples: a method wherein a test substance is administered to the aforementioned DAP12 knockout mouse, and the expression of myelin basic protein in a tissue, an organ, or a cell derived from the non-human animal is measured and assessed; a method wherein a test substance is administered to the aforementioned DAP12 knockout mouse, and the development of myelinogenesis and the extent of demyelination of the non-human animal are measured and assessed; a method wherein a test substance is administered to the aforementioned DAP12 knockout mouse, and acoustic stimuli and/or acoustic prepulse inhibition of the non-human animal are measured and assessed. In addition, it is preferable to compare and assess the DAP12 knockout mouse and the syngeneic wild-type littermate mouse in the above-mentioned screening.

Candidate substances of a developmental promoter or a developmental suppressor of oligodendrocytes that can be obtained by the screening method for a developmental promoter or a developmental suppressor of oligodendrocytes, a promoter or a suppressor of myelinogenesis of the present invention are exemplified by various low molecular weight compounds such as, but not limited to, inhibitors of tyrosine phosphatases, activators of tyrosine kinases, among others. As for the therapeutic agents for neuropsychiatric disorders such as Nasu-Hakola disease, dementia, schizophrenia, schizotypal personality disorders, obsessive-compulsive disorders, Huntington's disease, Tourette's syndrome, and other diseases, of the present invention, it is not particularly restricted as long as they are the therapeutic agents containing a developmental promoter or a developmental suppressor of oligodendrocytes, a promoter or a suppressor of myelinogenesis that can be obtained by the above-mentioned screening methods for a developmental promoter or a developmental suppressor of oligodendrocytes, promoter or suppressor of myelinogenesis, as an active ingredient. The above-mentioned neuropsychiatric disorders can be treated by administering the therapeutic agents to mammalian animals and the like with an appropriate amount and in an appropriate manner.

The non-human animal model of myelinogenesis developmental disorders of the present invention can be useful for the following models: a model wherein developmental disorder of myelinogenesis in central nervous system occurs; a model wherein the process of myelinogenesis is investigated; and a model wherein the onset of neuropsychiatric disorders, such as dementia caused by demyelination are investigated. Using these experimental animal models, it is possible to analyze the mechanisms leading to neuropsychiatric disorders, such as Nasu-Hakola disease, dementia, schizophrenia, schizotypal personality disorders, obsessive-compulsive disorders, Huntington's disease and Tourette's syndrome, among others, and to develop preventive methods for the progress of neuropsychitric disorders and a therapeutic method for neuropsychiatric disorders.

The therapeutic compositions can be exemplified by those obtained by the screening methods of the present invention. Using the non-human animal model of oligodendrocyte developmental disorders, the non-human animals can screen for therapeutic compositions useful in treating neuropsychiatric disorders. The therapeutic composition may contain a pharmaceutically acceptable carrier or a diluent, an additive agent, among others. The carrier or diluent can be particularly exemplified by the following: a stabilizing agent such as SPGA; carbohydrates such as sorbitol, mannitol, starch, sucrose, glucose, dextran and the like; proteins such as albumin, casein and the like; protein-containing substances such as bovine sera, skim milk and the like; buffer solutions such as phosphate buffer solution, physiological saline, water and the like. The additive agent can be exemplified by polypeptides of low molecular weight (less than approximately 10 residues), proteins, amino acids, carbohydrate containing glucose or dextran, chelating agents such as EDTA and the like, protein stabilizing agents, inhibitors or suppressors of microorganism proliferation and the like, but they are not limited to these examples.

Preferable forms for these therapeutic compositions are forms which can be administered orally, intravenously, intraperitoneally, intranasally, intracutaneously, subcutaneously, intramascularly and the like. Effective doses to be administered can be determined accordingly by considering the types and compositions of such pharmaceutical agents or pharmaceutical compositions, the administration methods, the age and body weight of a patient, etc. It is preferable to administer them one or a few times a day. When administered orally, it is ordinarily administered through the formulations prepared by mixing with a carrier for formulation. Here, a substance which is usually used in the formulation field, and which does not react with the compositions of the present invention is used as a carrier for formulation.

Further, dosage forms can be particularly exemplified by tablets, capsules, granules, powder, syrup, suspension agent, suppository, ointment, cream, gel, patch, inhalant, injectable solution, etc. These formulations are prepared by ordinary protocols, and particularly, liquid formulation can be dissolved or suspended into water or other appropriate media when used. Tablets and granules may be coated by a known method. Injectable solution can be prepared by dissolving the therapeutic composition of the present invention into water, however, it may also be dissolved into physiological saline or glucose solution according to need, and buffer agent or preservation agent may be further added. These formulations may also contain other ingredients of therapeutic value.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilizing agent(s), and other carrier agents that may aid or increase entry of the pharmaceutical composition or agent into a preferred tissue site (such as for example a lipid delivery system).

The present invention will be particularly explained below with the following examples, however, the scope of the present invention will not be limited to these examples.

EXAMPLES

Example 1

Generation of DAP12 Knockout$^{-/-}$ Mice

DAP12 knockout mice were generated by hybridizing the 129/SvJ (H-$2^b$) and C57BL/6 (B6, H-$2^b$) as described previously (Cell 76, 519-529, 1994). DAP12 genomic DNA was isolated from the 129/SvJ mouse genomic library (Stratagene), and 5.1 kb of Bam HI fragment containing the promoter region and exons 1-3 of the DAP12 gene was substituted by the neo$^r$ cassette (Stratagene). A targeting vector was constructed by inserting a herpes simplex virus thymidine kinase (HSV-TK) as a negative selectable marker. In addition, the neo$^r$ cassette contained 5.1 and 1.2 kb of homologous flanking sequences. As a result of homologous recombination after this vector was linearized and inserted into ES cells (RW4) by electroporation, homologous ES cell recombinants were obtained at a frequency of 7.1%. ES clones were isolated from the above-mentioned homologous recombinants, and neomycin resistant ES clones were screened for G418 and GANC (gancyclovir), and were subsequently confirmed by Southern blotting. Genomic DNA was isolated from the homologous recombinants and digested with KpnI. It was then confirmed that a targeting allele including neo$^r$ cassette was inserted. These confirmed ES clones were microinjected into blastocysts to generate chimeric mice, and such generated chimeric mice were intercrossed with a wild-type C57BL/6 mouse (Charles River Laboratories). Heterozygous mice were obtained by breeding them in a environmentally controlled and specific pathogen-free facility. These heterozygous mice were further intercrossed to obtain homozygous mice, and deficient mice whose DAP12 genes were deficient on their chromosomes and their wild-type counterparts were generated. The DAP12 knockout mice of the present invention were healthy without particular aberrations at least up to 10-months of age, as described previously (Immunity 13, 345-353, 2000; Immunity 13, 355-364, 2000). It was then examined whether DAP12-expression was ablated in a DAP12 knockout mouse obtained herein by Southern blotting, wherein genomic DNAs obtained from the tail tip of the mouse such as DAP12$^{+/+}$, DAP12$^{+/-}$, DAP12$^{-/-}$, etc., were digested with KpnI. A probe of the region shown in FIG. 1a was used (FIG. 1b).

Bone marrow mast cells (BMMCs) were prepared from DAP12$^{+/+}$ and DAP12$^{-/-}$ mice as described previously (Cell 76, 519-529, 1994), and further examined by immunoblot analysis Protein extracted from the mast cells (corresponding 2.5×10$^5$ cells per lane) and anti-rabbit DAP12 antiserum (diluted at 1:500) was prepared by the method described previously (Cell 70, 351, 1992) (FIG. 1c). DAP12 protein was not detected in cells derived from DAP12$^{-/-}$ mice. It is reported that the DAP10 gene, which is a cell surface adaptor protein of the same species as the above-mentioned DAP12 gene, is located on the same chromosome DNA strand positioned tail-to-tail with the DAP12 gene, which is merely 0.1 kb apart (J. Immunol. 163, 4651-4654, 1999; Science 285, 730-732, 1999). Reverse transcription polymerase chain reaction (RT-PCR) was conducted to examine whether the above-mentioned DAP12 knockout affected the DAP10 gene. Each cDNA was synthesized by using 3 μg of total RNA extracted from the above-mentioned DAP12$^{+/+}$ or DAP12$^{-/-}$ mice-derived bone marrow mast cells (BMMCs), and a reverse transcriptase ReverTra Ace (TOYOBO). Each cDNA was amplified by PCR method using the primers described below, and a signal of DAP10 was confirmed. As a result, although the expression of DAP10 was normal in DAP12$^{-/-}$ mice, the expression of DAP12 mRNA was not recognized. As for the primer specific to the above-mentioned DAP12, 5'-atgggggctctggagccct-3' (Seq. ID No. 1; P1) and 5'-tcatctgtaatattgcctct-3' (Seq ID No. 2; P2) were used, and as for primers specific to DAP10, 5'-atggac-cccccaggcta-3' (Seq ID No. 3; P3) and 5'-tcagcctctgccaggca-3' (Seq ID No. 4; P4) were used.

Example 2

Status of Neurons, Neurofilaments, and Astrocytes in DAP12 Knockout Mice

DAP12 knockout mice (−/−) or wild-type mice (+/+) at three months of age were anesthetized, and perfused with acid-alcohol solution (95% ethanol/5% acetic acid; vol %). Brains were isolated from these mice, and fixed overnight with acid-alcohol solution. Fixed brains underwent a standard protocol for paraffination (treating fixed brains for 1-2 hours each with 100% ethanol, methyl benzonate, xylene, xylene-paraffin, or paraffin solution), then embedding in Paraffin. Embedded brains were sliced 10 μm thick using a microtome, and underwent a standard protocol for deparaffination (xylene, 100% ethanol, 90% ethanol, 70% ethanol, and phosphate buffered saline). Intracellular peroxidase activity was suppressed with 3% $H_2O_2$ for 10 minutes, and rinsed again with PBS. Slices were treated in PBS containing primary antibodies including 0.5% skim milk (DIFCO) at 37° C. for 1 hour. They were subsequently washed three times with PBS at 37° C. for 3 minutes with shaking. The secondary antibodies (1:100 dilution of HRP-labeled anti-rabbit IgG antibody)(MBL) were added to PBS containing 0.5% skim milk and incubated at 37° C. for 50 minutes.

Figure 2:
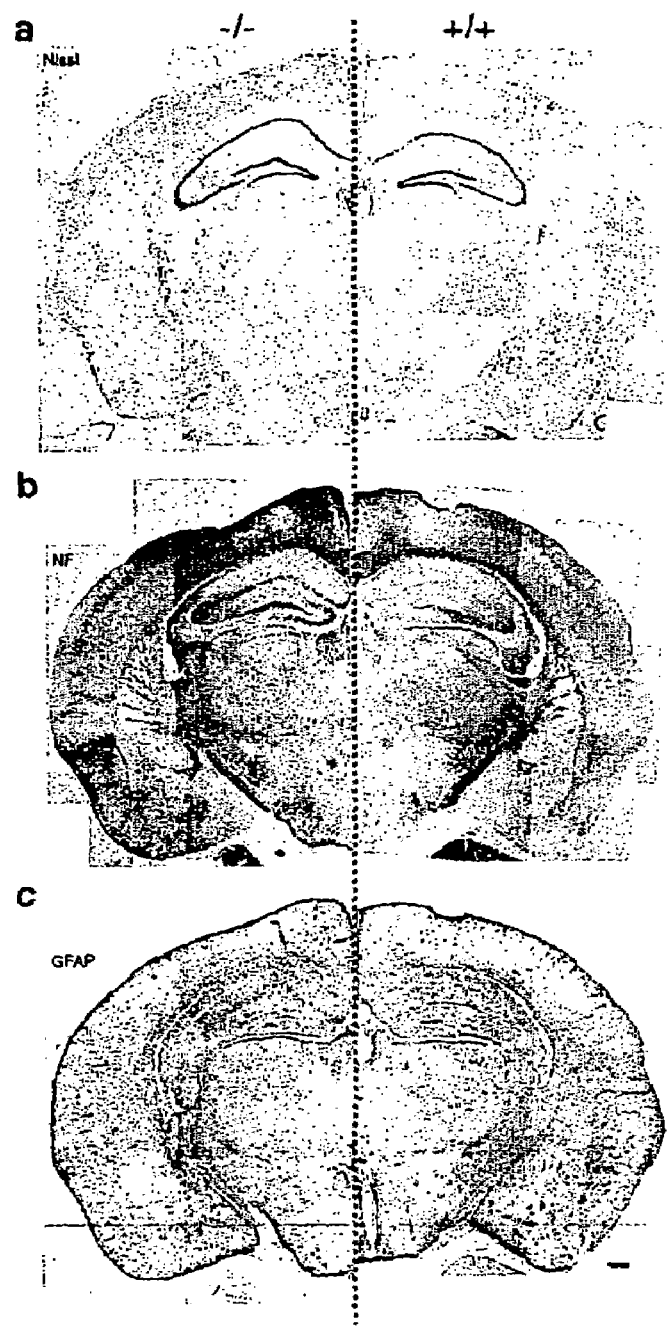
FIG. 2 shows neurons, neurofilaments, and astrocytes in the DAP12 knockout mouse and the wild-type mouse of the present invention.

The slices treated with the above-mentioned secondary antibodies were washed with PBS three times at 37° C. for 3 minutes with shaking, and were visualized by immunostaining using DAB (diamino-benzidine; Wako Pure Chemical Industries, Ltd.) as described previously (Neurosci. Res. 37, 21-31, 2000). Nissl staining was conducted to the above-mentioned brain slices using Methyl green instead of a primary antibody for comparison (FIG. 2a; Nissl). These results are shown in FIG. 2. The scale bar in the figure indicates 250 μm. These results show no significant change in neurons (FIG. 2a; Nissl), neurofilaments (FIG. 2b; NF), and astrocytes (FIG. 2c; GFAP) of DAP12 knockout mice (−/−) and wild-type mice (+/+).

Example 3

Reduction of Myelin Basic Protein and CNS Hypomyelinosis in DAP12$^{-/-}$ Mice

Figure 3:
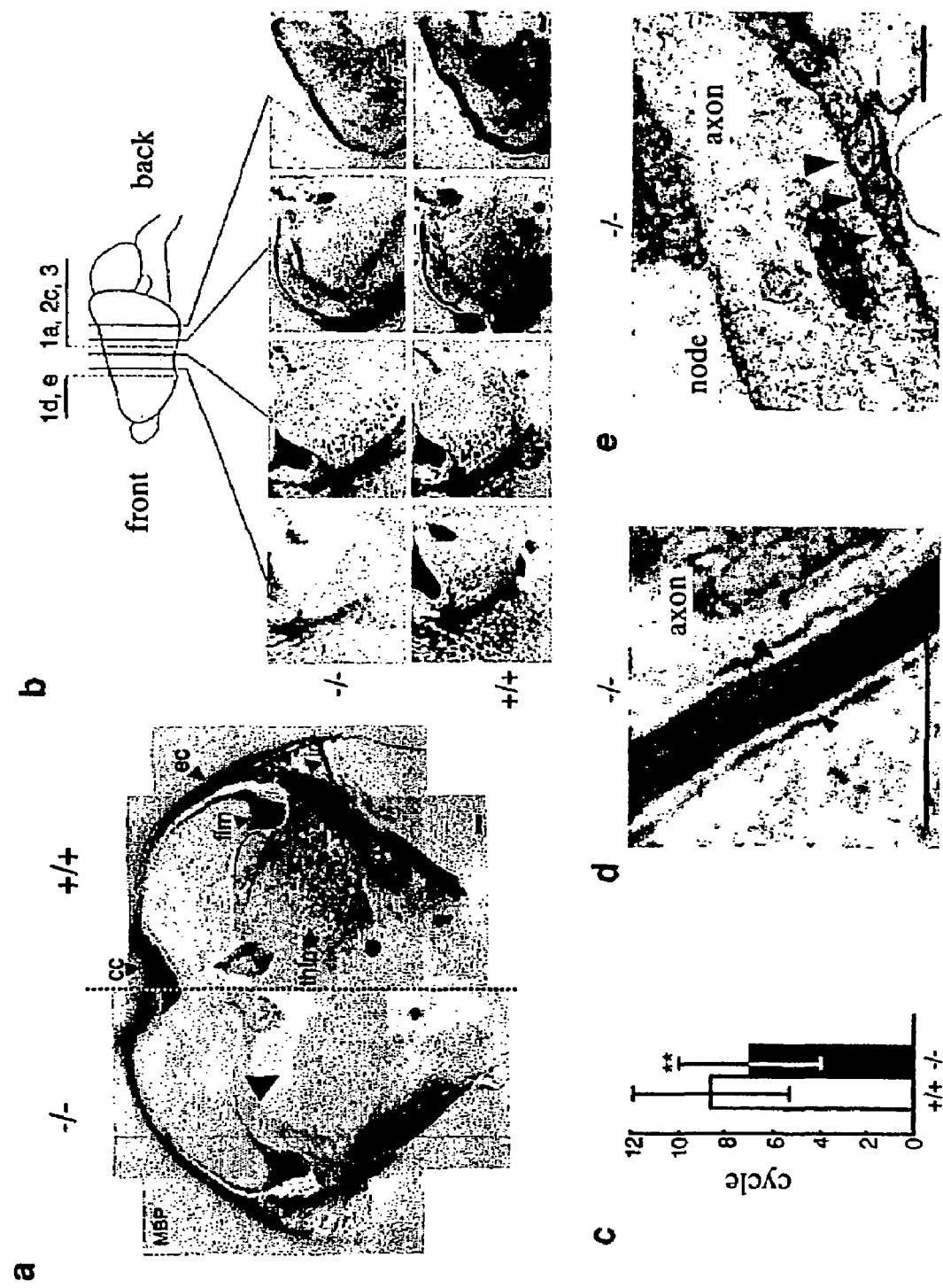
FIG. 3 shows the results of the reduction of myelin basic protein and CNS hypomyelinosis in the DAP12 knockout mouse and the wild-type mouse of the present invention.

Using a rabbit anti-mouse MBP antibody (Nichirei) as a primary antibody, the area indicated by the dashed line "a" (FIG. 3a) or lined area (FIG. 3b below) of the coronal brain slices shown in the schematic side view of FIG. 3b were stained and visualized in the same manner as described in Example 2. The results are shown in FIGS. 3a and b. In FIG. 3a, "cc" corresponds to the corpus callosum, "ec" for the external capsule, "ic" for the internal capsule, "fim" for the fimbria, "thlm" for the thalamus, respectively. The scale bar indicates 250 μm. In addition, the upper drawing of FIG. 3b shows the rough profile of a mouse, and the shaded area therein refers to the cerebrum. "Cp" in the FIG. 3b means the caudate nucleus, and the scale bar indicates 250 μm. These results show that the staining of myelin basic protein (MBP), a major and specific component of myelin, was reduced in part of brain, being especially accentuated in the thalamus (indicated by the large arrowhead in the figure), in 3-month-old DAP12 knockout mice.

The reduction of MBP staining in the thalamus as mentioned above was more noticeable in the frontal lobe of cerebrum including the caudate nucleus than in the posterior region of DAP12 knockout mice at 3 months as well as 1.5 months of age. Immunoblot analysis showed the mean intensity of MBP signals in myelin fractions prepared from whole brains of six DAP12 knockout mice at 7 months of age was 74% of that of wild-type mice. These results strongly indicated that the amount of MBP in central nervous system (CNS) myelin was reduced to a greater extent in adult DAP12 knockout mice than in wild-type mice, especially in the frontal lobe of cerebrum and the thalamus, without any defects in neurons, neurofilaments, and astrocytes. It is well known that myelin is a mutilamellar membrane structure, which wraps around axons, accelerating the conduction of nerve impulses, and serving as an important insulator for axon (Science 280, 1610-1613, 1998). In CNS, myelin is synthesized by oligodendrocytes, and the formation of myelin sheath takes place immediately after birth. Many autopsy cases for human NHD patients showed frontally accentuated deficiency of myelin and thalamus degeneration (Acta Psychiatr. Scand. Suppl. 232, 1-173, 1972; Neuropathol. Appl. Neurobiol. 26, 98-101, 2000).

It is known that MBP deficient mice (known as shiverers) result in severe hypomyelinosis of CNS axons accompanied by seizures with generalized tremors culminating in premature death within 3 months (Neurosci. Lett. 12, 113-118, 1979). The reduction of MBP observed in adult DAP12 knockout mice (−/−) (FIG. 3a, b) is attributed to hypomyelinosis in the animals due to incomplete myelination, or demyelination caused by other reasons, such as normal turnover mechanism or inflammation. Therefore, the caudate nucleus in frontal lobe of cerebrum was collected from 3-month-old DAP12 knockout (−/−) mice, and treated in 0.1 M of sodium cacodylate containing 1% of $O_sO_4$, then embedded in Epon 812. Ultrathin slices (85 nm) of cerebrum were examined with Hitachi H-7100 system. As a result, obvious hypomyelinosis was recognized (FIG. 3c). Enumerating the major dense lines of myelin sheaths showed a significant reduction in multiplicity of myelin lamellae of the −/− mice (mean±s.d.; 6.98±3.16, 8.64±3.31 for −/−, +/+ mice, respectively, n=128, "**" means P=0.0001). On the other hand, because no-laxation could be particularly seen on the major dense lines (dashed lined area "b" of the coronal brain slices in the schematic side view of brain shown in FIG. 3b upper part), it was confirmed that each lamellae forms the compaction (indicated by the arrowhead in FIG. 3d), and no signs for demyelination of the −/− mouse was recognized in the peripheral region of the node of Ranvier (FIG. 3e, arrowhead). FIG. 3e is a result of observation at magnification of 40,000, and the scale bars in FIGS. 3d and e indicate 250 nm.

Example 4

Expression of DAP12 Protein in Oligodendrocytes In vivo and In vitro

With respect to the relation between demyelination and DAP12 deficiency, Paloneva and coworkers clarified the expression of mRNA of DAP12 in primary cultures of mouse-derived microglial cells, astrocytes, and neurons by Northern blotting and RT-PCR analysis (Nature Genet. 25, 357-361, 2000). However, it has not been clarified whether DAP12 protein is actually expressed in the above-mentioned cells and in oligodendrocytes, which are classified as macroglial cells in CNS. Therefore, oligodendrocytes in primary cultures derived from the wild-type mice and the DAP12 knockout mice were analyzed by immunoblotting. The oligodendrocytes were cultured in the manner as described below.

Mouse-derived oligodendroglias were cultured as described previously (Cell 76, 519-529, 1994). Brains from newborn wild-type mice (+/+) and DAP12 deficient mice (−/−) were dissected, and oligodendroglias were prepared by the method for separate cultures (J. Cell Biol. 85, 890-902, 1980). Cells were plated in approximately 10 ml of Dulbecco's modified Eagle's medium (DMEM) containing 10% fetal bovine serum (FBS) per brain, then oligodendrocytes attached to the astroglial monolayer were dissociated and purified by orbital shaking as described previously (Dev. Biol. 83, 311-327, 1981). Over 95% of purified cells were positive for O4, an oligodendrocyte-specific marker. The remaining astrocytes cell layers were dissociated and purified with trypsin/EDTA. Approximately 20% of these astrocytes fractions were confirmed to contain $O4^+$ oligodendrocytes by flow cytometry.

Figure 4:
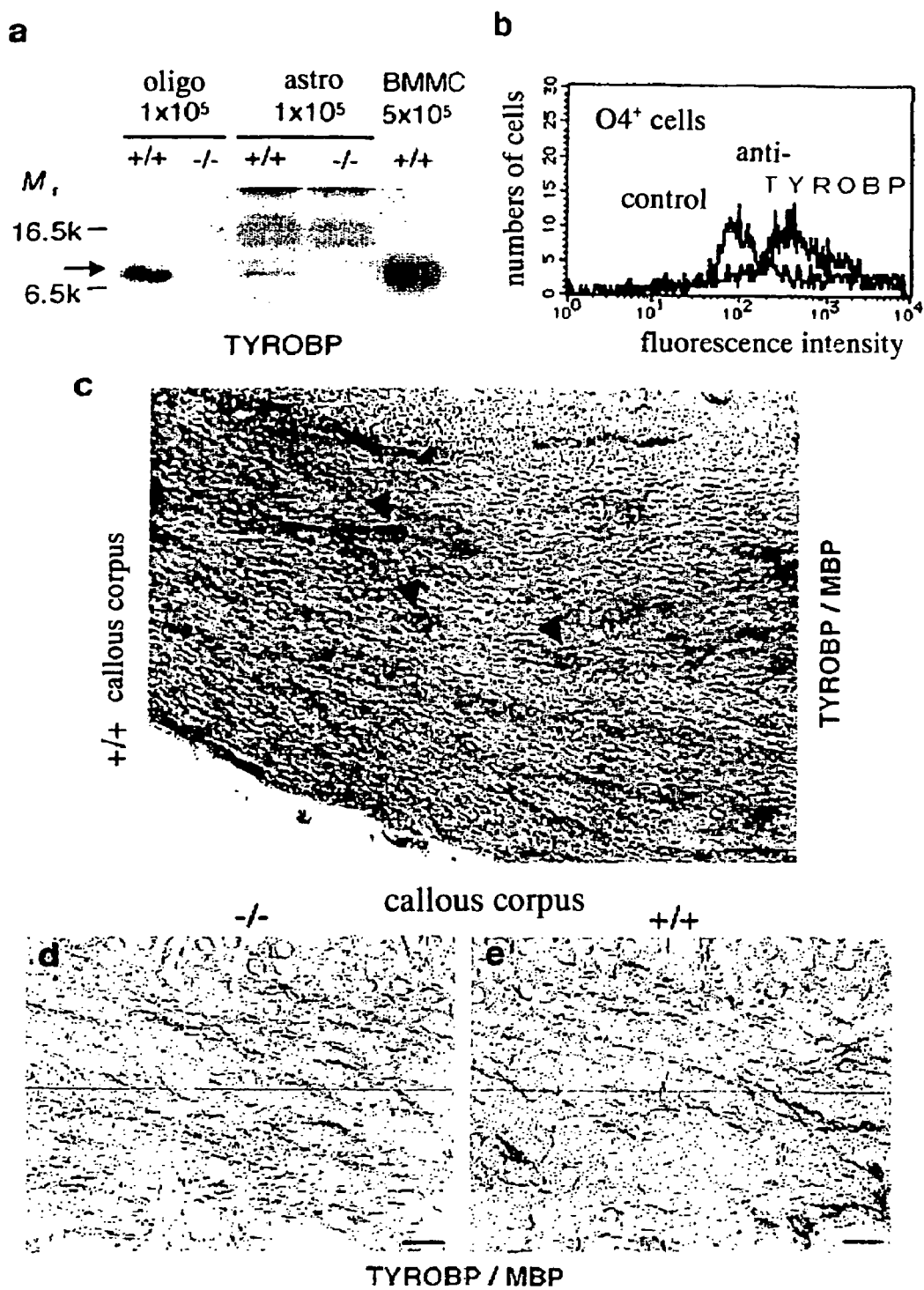
FIG. 4 shows the results of the expression of DAP12 protein in oligodendrocytes in vitro or in vivo in the DAP12 knockout mouse and the wild-type mouse of the present invention.

Oligodendrocytes (Oligo) and Astrocytes (Astro) were prepared respectively from the above-mentioned purified wild-type or DAP12 deficient mice, then immunoblot analysis was conducted using protein extracted from those cells ($1 \times 10^5$ cells per lane) in the same manner as described in Example 2. Bone marrow mast cells (BMMC; $5 \times 10^5$ cells) prepared in Example 1 were used as positive controls. The results are shown in FIG. 4a. The arrow in the figure indicates the position of DAP12. From these findings, it was confirmed by the concentration measurement that signal intensity of DAP12 in wild-type mouse-derived oligodendrocytes was almost comparable to the same number of mast cells. DAP12 mRNA signals were detected by RT-PCR analysis in the oligodendrocytes, as described in Example 1.

The aforementioned purified oligodendrocytes derived from wild-type mice were further purified using a magnetic cell sorter (Miltenyi) and an anti-O4 monoclonal antibody. A small hole was made on the membrane of the obtained $O4^+$ cells, then cells were stained using purified rabbit anti-DAP12 IgG antibodies or a rabbit IgG labeled with fluorescein isothiocyanate (FITC) as a control. As a result of the flow cytometric analysis, it was confirmed that DAP12 is expressed in the oligodendrocytes positive for O4 antigens (FIG. 4b).

In the cerebrum derived from 3-month-old wild-type mice (+/+), 10-day-old (in infancy) wild-type mice (+/+), or 10-day-old (in infancy) DAP12 knockout mice (−/−), double staining profiles against DAP12 and MBP were examined. Brain slices (shown by the dashed lined area of coronal brain slices in the schematic side view of brain in FIG. 3b, upper section) were generated from each of the above-mentioned mouse in the same manner as described in Example 2, and incubated using the anti-DAP12 antibody as a primary antibody overnight at 4° C. After an HRP labeled anti-rabbit IgG antibody as a secondary antibody was reacted, brain slices were immunostained with DAB. After the staining, brain slices were washed with PBS, then stirred in 0.1 M of glycine-HCl buffer (pH2.2) for 1 hour to remove the antibody. Thereafter, brain slices were reacted with a rabbit anti-mouse MBP antibody as a primary antibody at 37° C. for 1 hour, and HRP labeled anti-rabbit IgG antibody as a secondary antibody. Blue staining was conducted with 4-chloro-1-naphthol (Wako Pure Chemical Industries, Ltd.). The results are shown in FIG. 4c-e. The arrowheads in FIG. 4c indicate the cells that are double stained for DAP12 and MBP, and the scale bars in FIG. 4c-e indicate 25 μm.

Based on the above-mentioned results, in adult wild-type mice of 3-month-old, the corpus callosum (FIG. 4c), the fimbria, the external and internal capsules, and the thalamus (FIG. 5c) were strongly positive for proteins of both DAP12 and MBP. Therefore, these proteins are co-expressed. As a result of identification of the cells expressing both DAP12 and MBP in the regions (FIG. 4c), it was revealed that the DAP12 expression of oligodendrocytes in CNS of adult mice is accompanied by MBP expression. In contrast, neither the reduction in MBP staining of the corpus callosum of 10-day-old DAP12 knockout mice (FIG. 2d), nor the DAP12 co-expression anywhere in CNS of 10-day-old wild-type mice (FIG. 2e) was detected. These observations suggest that early formation of the myelin sheath in the developing brain is normal under the DAP12 deficiencies and that the DAP12 expression is under developmental control. Therefore, in the DAP12 knockout mice, hypomyelinosis should occur at later developmental phases up to 1.5 months of age at most.

Example 5

Coupling of DAP12 Expression and Myelinogenesis

Figure 5:
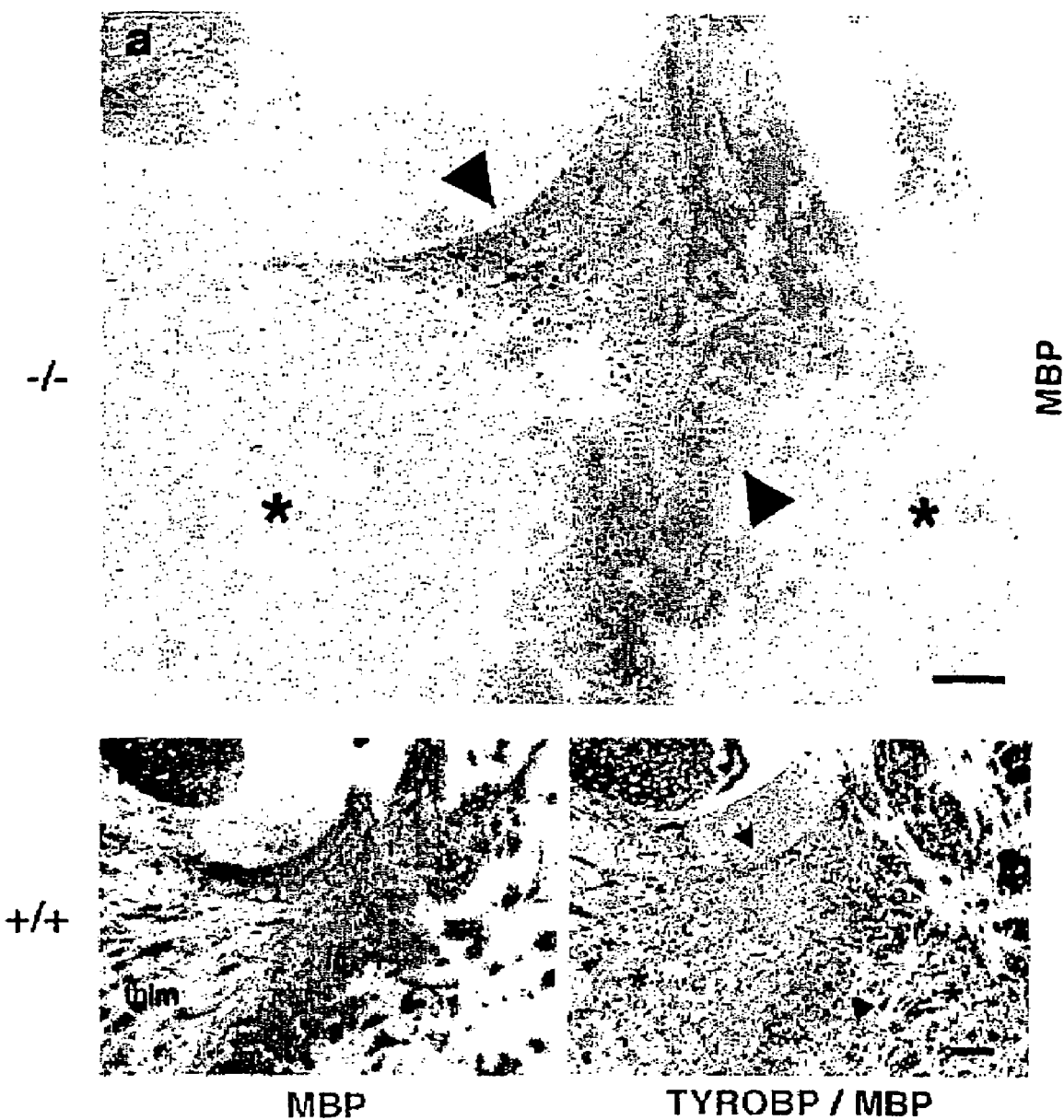
FIG. 5 shows the results of DAP12 expression and myelinogenesis in the DAP12 knockout mouse and the wild-type mouse of the present invention.

Brain slices including the internal capsule (ic) and the thalamus (thlm) regions (dashed lined area (a) of coronal brain slices in the schematic side view of brain shown in FIG. 3b upper section) were prepared from 3-month-old DAP12 knockout mice (−/−) (FIG. 5a) or wild-type mice (+/+) (FIGS. 5b and c), and the expression of MBP (FIGS. 5a and b), or the expression of MBP and DAP12 (FIG. 5c) was examined. MBP was examined in the same manner as described in Example 3, and the expression of MBP and DAP12 was as described in Example 4. The results are shown in FIG. 5. The arrowheads in the figure indicate the internal capsule of cerebrum, and the asterisk indicates the DAP12 positive region. Each scale bar corresponds to 100 μm. From these results, in 3-month-old (FIG. 5a) and 1.5-month-old DAP12 knockout mice (−/−), most of MBP positive oligodendrocytes were recognized in several regions, such as the internal capsule (the arrowhead in FIG. 5a), the fimbria, the thalamus, and the like of cerebrum. On the other hand, the oligodendrocytes in the brain of an adult wild-type mouse (+/+) were hardly identified by MBP staining in low magnified views due to their development of numerous MBP-positive dendrites (FIG. 5b). However, staining intensity of DAP12 in wild-type mice was most notable in the region of the internal capsule (indicated by arrowheads in FIG. 5c), where clusters of oligodendrocytes were found in DAP12 knockout mice (FIG. 5a). In contrast, it was confirmed that the expression of MBP is weak in DAP12 knockout mice (* mark in FIG. 5a) in the region where DAP12 strongly expressed in wild-type mice (* mark in FIG. 5c). These observations strongly suggest that formation of the myelin sheath by oligodendrocytes is intimately involved in the DAP12 expression. In DAP12 knockout mice, the oligodendrocytes that create the formation of the myelin sheath in wild-type mice were not activated. These results suggest that DAP12 in the CNS plays an important role in activation of the formation of the myelin sheath in the late developmental phase as well as in the maintenance phase.

Example 6

Deficiencies of Sensorimotor Gating in DAP12 Knockout Mouse

Figure 6:
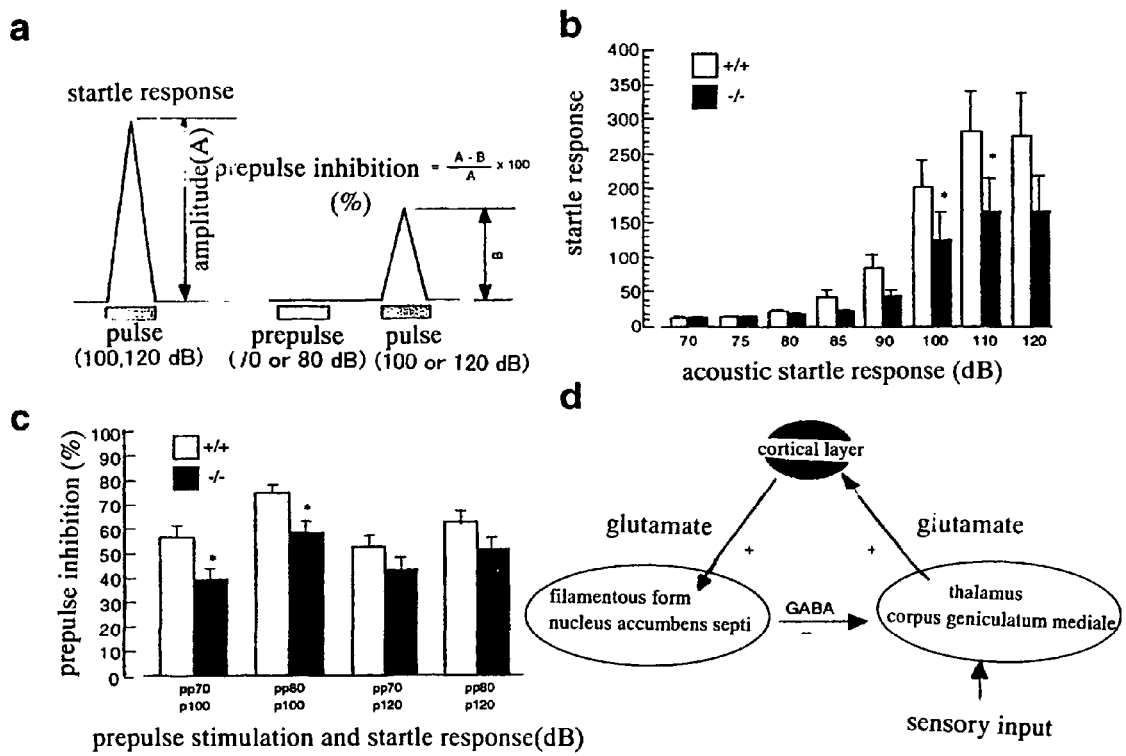
FIG. 6 shows the results of sensorimotor gating in the DAP12 knockout mouse and the wild-type mouse of the present invention.

The thalamus is one of the most important areas in the brain, which incorporates the impulses from every sensory organ and determines the subsequent responses by controlling nerve conductions. Therefore, thalamus-specific demyelination in DAP12 knockout mice could induce behavioral deficits. The DAP12 knockout mice used in the experiments herein, however, showed normal behaviors. Interestingly, it was previously reported that magnetic resonance imaging (MRI) of a NHD patient found reduced signal intensity in the thalamus and putamen (Rinsho Shinkeigaku 32, 444-446, 1992). We therefore examined acoustic startle response and prepulse inhibition in the DAP12 knockout mice at 5 months of age. Schematic view of acoustic startle response (the left side), and prepulse inhibition (the right side) are shown in FIG. 6a. Acoustic startle responses of mice were measured with the SR-LAB system (San Diego Instruments), and the background noise level in the chamber was 65 dB during the test. Wild-type mice (+/+) or DAP12 knockout mice (+/+) were placed into cylinders 10 minutes prior to the initial startle stimuli and were acclimated to the background noise. The maximum amplitude of startle response was measured by recording the amplitude of startle response for only 100 msecs from the startle stimuli initiated. In the acoustic startle response experiment, eight different types of startle stimuli (70, 75, 80, 85, 90, 100, 110, and 120 dB; 20 msec broad band burst) were used. Each stimulus was repeated 5 times in the same order. The experiments were conducted with an interval of an average of 40 secs. The results are shown in FIG. 6b. Measurement value in FIG. 6b, is shown as mean±s.e.m. (n=10, "*" means P<0.05). As shown in FIG. 6b, DAP12 knockout mice showed significantly lower levels of startle responses in general compared to wild-type mice [F(1,18)=5.790, P<0.05]. It was found that this difference was mainly caused by the reduction of startle response in 100 and 110 dB. Therefore, abnormal responses to acoustic stimuli in the DAP12 knockout mice at 5 months of age were revealed.

In the acoustic prepulse inhibition experiment, each session consisted of seven different types of stimuli: no stimulus, startle stimulus trials only, or a prepulse proceeded by the startle stimulus. No response was seen in mice in any stimuli. Two startle trial types were 20 msec startle stimuli of either 100 or 120 dB. Combinations of four different acoustic prepulses with acoustic startle stimuli for 100 msec were performed before the onset of the startle stimulus. Each 20 msec prepulse stimulus (either 70 or 80 dB) was presented before both acoustic startle stimuli. Seven different types of stimuli were presented nine times in random order. The trials were conducted with an interval of an average of 40 secs. Percentage prepulse inhibition of a startle response was calculated using the formula as described below. The results are shown in FIG. 6c. Besides, the data were analyzed with repeated measurements using two-way ANOVA to determine the overall significance, then the differences among the groups were determined by Student's t-test, and shown as mean±s.e.m. (n=10, "*" means P<0.05). As a result, DAP12 knockout mice displayed significantly lower suppression levels of acoustic prepulse inhibition [F (1,18) =5.061, P<0.05], which was particularly observed in startle stimuli of 100 dB.

Formula 1:

$$1 - \frac{\text{startle response on acoustic prepulse and startle stimulus trials}}{\text{startle response alone trials}} \times 100$$

The acoustic startle reflex is known to be a simple neural circuit, receiving inputs from the thalamus and arising from diverse cortical, midbrain, or hindbrain centers. Prepulse inhibition of startle response, which is a modification of the startle response by a weak prepulse, is a measure for sensorimotor gating, which coincides with a theoretical circuit of central inhibitory process in CNS by which an organism filters the flow of information via thalamus and gates the threshold of its subsequent behavior (J. Neurosci. 12, 4501-4509, 1992; Brain Res. 499, 7-17, 1989; Brain Res. Bull. 43, 219-228, 1997) (FIG. 4d). An impairment in sensorimotor gating results in sensory inundation, cognitive fragmentation, and attention deficits, as seen in several human neuropsychiatric disorders including dementia, schizophrenia, schizotypal personality disorders, obsessive-compulsive disorders, Huntington's disease and Tourette's syndrome, among others. Therefore, DAP12 knockout mice are considered to induce lower startle response and impaired sensorimotor gating, presumably due to the thalamus-specific hypomyelinosis. Although the possibility that the DAP12 knockout mice develop more severe abnormalities in behavior or learning ability in the more aged phases is not excluded, it has become evident that they show psychiatric symptoms, similar to schizophrenia in humans, as early as 5 months of age.

The invention is further described by the following numbered paragraphs:

1. A non-human animal model of oligodendrocyte developmental disorders whose DAP12 (DNAX Activation Protein 12) gene function is deficient on its chromosome, and that shows an oligodendrocyte developmental disorder.

2. The non-human animal model of oligodendrocyte developmental disorders according to paragraph 1, wherein a myelinogenesis developmental disorder has been initiated.

3. The non-human animal model of oligodendrocyte developmental disorders according to paragraph 1 or 2, wherein a neuropsychiatric disorder has been induced.

4. The non-human animal model of oligodendrocyte developmental disorders according paragraph 3, wherein the neuropsychiatric disorder is Nasu-Hakola disease, dementia, schizophrenia, schizotypal personality disorders, obsessive-compulsive disorders, Huntington's disease or Tourette's syndrome.

5. The non-human animal model of oligodendrocyte developmental disorders according to any of paragraphs 1 to 4, wherein the non-human animal is a mouse.

6. A screening method for a developmental promoter or a developmental suppressor of oligodendrocytes, wherein a test substance is administered to the non-human animal model of oligodendrocyte developmental disorders according to any of paragraphs 1 to 5, or a test substance is contacted with a tissue, an organ, or a cell derived from the animal.

7. A screening method for a developmental promoter or a developmental suppressor of oligodendrocytes, wherein a tissue, an organ, or a cell derived from the non-human animal model of oligodendrocyte developmental disorders according to any of paragraphs 1 to 5, is contacted with a test substance, and the expression of myelin basic protein in the cells is measured and assessed.

8. A screening method for a developmental promoter or a developmental suppressor of oligodendrocytes, wherein a test substance is administered to the non-human animal model of oligodendrocyte developmental disorders according to any of paragraphs 1 to 5, and the expression of myelin basic protein in a tissue, an organ, or a cell derived from the non-human animal is measured and assessed.

9. A screening method for a developmental promoter or a developmental suppressor of oligodendrocytes, wherein a test substance is administered to the non-human animal model of oligodendrocyte developmental disorders according to any of paragraphs 1 to 5, and the development of myelinogenesis or the extent of demyelination in the animal is measured and assessed.

10. A screening method for a developmental promoter or a developmental suppressor of oligodendrocytes, wherein a test substance is administered to the non-human animal model of oligodendrocyte developmental disorders according to any of paragraphs 1 to 5, and acoustic stimuli and/or acoustic prepulse inhibition of the non-human animal are measured and assessed.

11. The screening method for a developmental promoter or a developmental suppressor of oligodendrocytes according to any of paragraphs 7 to 10, wherein a non-human animal whose DAP12 gene function is deficient on its chromosome and a wild-type non-human animal are compared and assessed.

12. The screening method for a developmental promoter or a developmental suppressor of oligodendrocytes according to any of paragraphs 7 to 11, wherein the non-human animal is a mouse.

13. The screening method for a developmental promoter or a developmental suppressor of oligodendrocytes according to any of paragraphs 7 to 12, wherein the developmental processor or a developmental suppressor of oligodendrocytes is a promoter or a suppressor of myelinogenesis.

14. A developmental promoter or a developmental suppressor of oligodendrocytes that can be obtained by the screening method for a developmental promoter or a developmental suppressor of oligodendrocytes according to any of paragraphs 7 to 12.

15. A promoter or a suppressor of myelinogenesis that can be obtained by the screening method for a developmental promoter or a developmental suppressor of oligodendrocytes according to paragraph 13.

16. A screening method for a therapeutic agent for neuropsychiatric disorders, wherein the non-human animal model of oligodendrocyte developmental disorders according to any of paragraphs 1 to 5 is used for the screening of a therapeutic agent for neuropsychiatric disorders.

17. A therapeutic agent for neuropsychiatric disorders that can be obtained by the screening method for a therapeutic agent for neuropsychiatric disorders according to paragraph 16.

18. A diagnostic method for neuropsychiatric disorders, wherein symptoms of the non-human animal model of oligodendrocyte developmental disorders according to any of paragraphs 1 to 5 are utilized for diagnosis of neuropsychiatric disorders.

REFERENCES

Bakker, A. B. H., Hoek, R. M., Cerwenka, A., Blom, B., Lucian, L., McNeil, T., Murray, R., Phillips, J. H., Sedgwick, J. D., and Lanier, L. L.: "DAP12-Deficient Mice Fail to Develop Autoimmunity Due to Impaired Antigen Priming" (2000) Immunity 13: 345-353.

Chang, C., Dietrich, J., Harpur, A. G., Lindquist, J. A., Haude, A., Loke, Y. W., King, A., Colonna, M., Trowsdale, J., and Wilson, M. J.: "KAP10, a Novel Transmembrane Adapter Protein Genetically Linked to DAP12 but with Unique Signaling Properties" (1999) J. Immunol. 163: 4651-4654.

Dupouey, P., Jacque, C., Bourre, J. M., Cesselin, F., Privat, A., and Baumann, N.: "Immunochemical studies of myelin basic protein in shiverer mouse devoid of major dense line of myelin", (1979) Neurosci. Lett. 12: 113-118.

Griffiths, I., Klugmann, M., Anderson, T., Yool, D., Thomson, C., Schwab, M. H., Schneider, A., Zimmermann, F., McCulloch, M., Nadon, N., and Nave, K. A.: "Axonal Swellings and Degeneration in Mice Lacking the Major Proteolipid of Myelin" (1998) Science 280: 1610-1613.

Hakola, H. P.: "Neuropsychiatric and genetic aspects of a new hereditary disease characterized by progressive dementia and lipomembranous polycystic osteodysplasia" (1972) Acta. Psychiatr. Scand. Suppl. 232: 1-173.

Kaelin, W. G. Jr, Krek, W., Sellers, W. R., DeCaprio, J. A., Ajchenbaum, F., Fuchs, C. S., Chittenden, T., Li, Y., Farnham, P. J., Blanar, M. A., et al.: "Expression cloning of a cDNA encoding a retinoblastoma-binding protein with E2F-like properties". (1992) Cell. 70(2): 351-64.

Kobayashi, K., Kobayashi, E., Miyazu, K., Muramori, F., Hiramatsu, S., Aoki, T., Nakamura, I., and Koshino, Y.: "Hypothalamic haemorrhage and thalamus degeneration in a case of Nasu-Hakola disease with hallucinatory symptoms and central hypothermia" (2000) Neuropathol. Appl. Neurobiol. 26(1): 98-102.

Kodsi, M. H. and Swerdlow, N. R.: "Regulation of Prepulse Inhibition by Ventral Pallidal Projections" (1997) Brain Res. Bull. 43: 219-228.

Lanier, L. L., Corliss, B., Wu, J., and Phillips, J. H.: "Association of DAP12 with Activating CD94/NKG2C NK Cell Receptors" (1998) Immunity 8: 693-701.

Lanier, L. L., Corliss, B. C., Wu, J., Leong, C., and Phillips, J. H.: "Immunoreceptor DAP12 bearing a tyrosine-based activation motif is involved in activating NK cells" (1998) Nature 391: 703-707.

Mason, L. H., Willette-Brown, J., Anderson, S. K., Gosselin, P., Shores, E. W., Love, P. E., Ortaldo, J. R., and McVicar, D. W.: "Characterization of an Associated 16-kDa Tyrosine Phosphoprotein Required for Ly-49D Signal Transduction" (1998) J. Immunol. 160: 4148-4152.

Nasu, T., Tsukahara, Y., and Terayama, K.: "A lipid metabolic disease-'membranous lipodystrophy'—an autopsy case demonstrating numerous peculiar membrane-structures composed of compound lipid in bone and bone marrow and various adipose tissues". (1973) Acta Pathol Jpn. 23(3): 539-58.

Olcese, L., Cambiaggi, A., Semenzato, G., Bottino, C., Moretta, A., and Vivier, E.: "Human killer cell activatory receptors for MHC class I molecules are included in a multimeric complex expressed by natural killer cells" (1997) J. Immunol. 158: 5083-5086.

Paloneva, J., Kestilä, M., Wu, J., Salminen, A., Böhling, T., Ruotsalainen, V., Hakola, P., Bakker, A. B. H., Phillips, J. H., Pekkarinen, P., Lanier, L. L., Timonen, T., and Peltonen, L.: "Loss-of-function mutations in TYROBP (DAP12) result in a presenile dementia with bone cysts" (2000) Nature Genetics 25: 357-361.

Romanski, L. M. and LeDoux, J. E.: "Equipotentiality of thalamo-amygdala and thalamo-cortico-amygdala circuits in auditory fear conditioning" (1992) J. Neurosci. 12: 4501-4509.

Seiwa, C., Sugiyama, I., Yagi, T., Iguchi, T., and Asou, H.: "Fyn tyrosine kinase participates in the compact myelin sheath formation in the central nervous system" (2000) Neurosci. Res. 37(1): 21-31.

Shinohara, M., Motohashi, N., Fukuzawa, H., Akiyama, Y., and Kariya, T.: "A case of Nasu-Hakola's disease with T2-weighted MRI finding of reduced signal intensity in the thalamus and putamen" (1992) Rinsho Shinkeigaku 32(4): 444-6.

Smith, K. M., Wu, J., Bakker, A. B. H., Phillips, J. H., and Lanier, L. L.: "Cutting Edge: Ly-49D and Ly-49H Associate with Mouse DAP12 and Form Activating Receptors" (1998) J. Immunol. 161: 7-10.

Sommer, I., and Schachner, M.: "Monoclonal antibodies (01 to 04) to oligodendrocyte cell surfaces: an immunocytological study in the central nervous system" (1981) Dev Biol. 83(2): 311-27.

Takai, T., Li, M., Sylvestre, D., Clynes, R., and Ravetch, J. V.: "FcR gamma chain deletion results in pleiotrophic effector cell defects" (994) Cell. 76(3): 519-29.

Tomasello, E., Desmoulins, P. O., Chemin, K., Guia, S., Cremer, H., Ortaldo, J., Love, P., Kaiserlian, D., and Vivier, E.: "Combined Natural Killer Cell and Dendritic Cell Functional Deficiency in KARAP/DAP12 Loss-of-Function Mutant Mice" (2000) Immunity 13: 355-364.

Verloes, A., Maquet, P., Sadzot, B., Vivario, M., Thiry, A., and Franck, G.: "Nasu-Hakola syndrome: polycystic lipomembranous osteodysplasia with sclerosing leucoencephalopathy and presenile dementia". (1997) J. Med. Genet. 34(9): 753-7.

Wu, M. F., Mallick B. N., and Siegel, J. M.: "Lateral geniculate spikes, muscle atonia and startle response elicited by auditory stimuli as a function of stimulus parameters and arousal state" (1989) Brain Res. 499(1): 7-17.

Wu, J., Song, Y., Bakker, A. B. H., Bauer, S., Spies, T., Lanier, L. L., and Phillips, J. H.: "An Activating Immunoreceptor Complex Formed by NKG2D and DAP10" (1999) Science 285: 730-732.

Having thus described in detail preferred embodiments of the present invention, it is to be understood that the invention defined by the appended claims is not to be limited to particular details set forth in the above description, as many apparent variations thereof are possible without departing from the spirit or scope of the present invention. Modifications and variations of the method and apparatuses described herein will be obvious to those skilled in the art, and are intended to be encompassed by the following claims.

We claim:

1. A transgenic mouse model showing Nasu-Hakola disease, wherein the transgenic mouse comprises a homozygous disruption in its endogenous DAP12 (DNAX Activation Protein 12) gene and shows hypomyelinosis of the thalamus, and wherein the homozygous disruption includes the promoter region and exons 1, 2, and 3.

2. The transgenic mouse model of claim 1, wherein the homozygous disruption in the DAP12 gene can be pheonotypically exhibited as a myelinogenesis developmental disorder.

3. The transgenic mouse model of claim 1 or 2, further showing a disease selected from the group consisting of dementia caused by Nasu-Hakola disease, schizophrenia caused by Nasu-Hakola disease, schizotypal personality disorders caused by Nasu-Hakola disease, obsessive-compulsive disorders caused by Nasu-Hakola disease, or Tourette's syndrome caused by Nasu-Hakola disease.

4. The transgenic mouse model of claim 1 or 2, further showing dementia caused by Nasu-Hakola disease.

5. The transgenic mouse model of claim 1, weherein the expression of myelin basic protein in the brain is weak in regions where DAP 12 is strongly expressed in wild-type mice.

6. The transgenic mouse model of claim 1, wherein the transgenic mouse exhibits an impairment in sensorimotor gating as compared to wild-type mice.

* * * * *

UNITED STATES PATENT AND TRADEMARK OFFICE
CERTIFICATE OF CORRECTION

PATENT NO. : 7,332,644 B2  Page 1 of 1
APPLICATION NO. : 10/712118
DATED : February 19, 2008
INVENTOR(S) : Toshiyuki Takai, Hiroaki Aso and Michihiro Fujiwara It is certified that error appears in the above-identified patent and that said Letters Patent is hereby corrected as shown below:

ON THE TITLE PAGE, should read

Item (75)    Toshiyuki Takai, "Sendai" --Miyagi-- (JP)

Col. 19, claim 2, line 28

The transgenic mouse model of claim 1, wherein the homozygous disruption in the DAP12 gene can be should read --phenotypically-- exhibited as a myelinogenesis developmental disorder.

Col. 20, claim 5, line 25 and 27, should read,

The transgenic mouse model of claim 1, --wherein-- the expression of myelin basic protein in the brain is weak in regions where DAP " "12 is strongly expressed in wild-type mice.

Signed and Sealed this

Fifteenth Day of July, 2008

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Primer P1 used for PCR amplicification of DAP12

<400> SEQUENCE: 1
atgggggctc tggagccct                                                       19

<210> SEQ ID NO 2
<211> LENGTH: 20
<212> TYPE: DNA
<213> ORGANISM: Artificial Sequence
<220> FEATURE:
<223> OTHER INFORMATION: Primer P2 used for PCR amplicification of DAP12

<400> SEQUENCE: 2
tcatctgtaa tattgcctct                                                      20

<210> SEQ ID NO 3
<211> LENGTH: 17
<212> TYPE: DNA
<213> ORGANISM: Artificial Sequence
<220> FEATURE:
```

```
<223> OTHER INFORMATION: Primer P3 used for PCR amplicification of DAP12

<400> SEQUENCE: 3
atggaccccc caggcta                                                    17

<210> SEQ ID NO 4
<211> LENGTH: 17
<212> TYPE: DNA
<213> ORGANISM: Artificial Sequence
<220> FEATURE:
<223> OTHER INFORMATION: Primer P4 used for PCR amplicification of DAP12

<400> SEQUENCE: 4
tcagcctctg ccaggca                                                    17
```